(12) United States Patent
Blough et al.

(10) Patent No.: US 10,899,699 B2
(45) Date of Patent: Jan. 26, 2021

(54) VINYLOGOUS PHENETHYLAMINES AS NEUROTRANSMITTER RELEASERS

(71) Applicant: RESEARCH TRIANGLE INSTITUTE, Research Triangle Park, NC (US)

(72) Inventors: Bruce Blough, Raleigh, NC (US); Ann Decker, Durham, NC (US); Richard Rothman, Ellicott City, MD (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 0 days.

(21) Appl. No.: 16/300,436

(22) PCT Filed: May 11, 2017

(86) PCT No.: PCT/US2017/032143
§ 371 (c)(1),
(2) Date: Nov. 9, 2018

(87) PCT Pub. No.: WO2017/197101
PCT Pub. Date: Nov. 16, 2017

(65) Prior Publication Data
US 2019/0225573 A1 Jul. 25, 2019

Related U.S. Application Data

(60) Provisional application No. 62/335,191, filed on May 12, 2016.

(51) Int. Cl.
| *A61K 31/135* | (2006.01) |
| *A61P 25/30* | (2006.01) |
| *C07C 211/28* | (2006.01) |

(52) U.S. Cl.
CPC .......... *C07C 211/28* (2013.01); *A61K 31/135* (2013.01); *A61P 25/30* (2018.01); *C07B 2200/07* (2013.01)

(58) Field of Classification Search
CPC ...... A61K 31/135; A61P 25/30; C07C 211/28
See application file for complete search history.

(56) References Cited

U.S. PATENT DOCUMENTS

| 6,337,351 B1 | 1/2002 | Dull et al. |
| 2006/0069261 A1 | 3/2006 | Bonneau et al. |
| 2010/0168094 A1 | 7/2010 | Binch et al. |
| 2013/0296271 A1 | 11/2013 | Sakai et al. |
| 2014/0171447 A1 | 6/2014 | Johnson |
| 2014/0336216 A1 | 11/2014 | Dvorak et al. |

FOREIGN PATENT DOCUMENTS

| EP | 0706994 A1 | 4/1996 | |
| EP | 2281801 A1 | 2/2011 | |
| WO | WO9833765 A | 8/1998 | |
| WO | WO0023418 A | 4/2000 | |
| WO | WO2004071445 A2 | 8/2004 | |
| WO | WO2006044823 A2 | 4/2006 | |
| WO | WO2008009613 A1 | 1/2008 | |
| WO | WO 2010/015029 | * 2/2010 | ............ A61K 31/19 |
| WO | WO2010121022 A1 | 10/2010 | |
| WO | WO2011103189 A1 | 8/2011 | |
| WO | WO2013048982 A1 | 4/2013 | |

OTHER PUBLICATIONS

Rothman et al., JPET, vol. 341, No. 1, pp. 251-262 (2012).*
Decker, A.M., et al., "The Biogenic Amine Transporter Activity of Vinylogous Amphetamine Analogs", "Med Chem. Commun.", 2016, pp. 1657-1663, vol. 7.
Liu, J., et al., "Catalytic Asymmetric Umpolung Allylation of Imines", "Journal of the Americal Chemical Society", 2016, pp. 13103-13106, vol. 138.
Yu, Z., et al., "Structure-Affinity Relationships (SARs) and Structure-Kinetics Relationships (SKRs) of Kv11.1 Blockers", "STN Chemical Abstracts", 2015, p. AN2015:1100250 CAPLUS.
Salvant,, J.M., et al., "Regioselective Base-Mediated Cyclizations of Mono-N-Acylpropargylguanidines", "STN Chemical Absracts", 2017, p. AN2017:885550 CAPLUS.
Duffey, M.O., et al., "Discovery of a Potent and Orally Bioavailable Benzolactam-Derived Inhibitor of Polo-Like Kinase 1", "STN Chemical Abstracts", 2011, p. AN2011:1443586 CAPLUS.
Kwatra, M.M., et al., "Acetylenics, 2-Synthesis and Pharmacology of Certain N1N-Dailkyl-3-phenylpropyn-2-amines and Some Analogs with Tryptamine-like Behavioral Effects in Mice", "STN Chemical Abstracts", 1978, p. AN1978:83447 CAPLUS.
Rodrigues, N., et al., "Synthesis and Structure-Actiity Relationship Study of Substituted Caffeate Esters as Antinociceptive Agents Modulating the TREK-1 Channel", "STN Chemical Abstracts", 2014, p. AN2014:367344 CAPLUS.
Ren, Y., et al., "Synthesis and Antiarrhythmic Activity of (Erythro)-phenylpropanediolamine Compounds", "STN Chemical Abstracts", 1997, p. AN:1997:803082 CAPLUS.
Dewal, M.B., et al., "Thienol(2,3-d)pyrimidinedione Derivatives as Antibacterial Agents", "STN Chemical Abstracts", 2012, p. AN2012:630616 CAPLUS.
Chemical Abstracts, "4-Penten-2-Amine, 5-Phenyl-", "STN Express", Apr. 18, 1987, p. RN:107638-85-7.

(Continued)

*Primary Examiner* — Alicia L Otton

(74) *Attorney, Agent, or Firm* — Hultquist, PLLC; Steven J. Hultquist

(57) ABSTRACT

The disclosure provides monoamine neurotransmitter releaser and/or monoamine uptake inhibitor compounds having biogenic amine transporter activity but lacking substantial activity at 5-HT$_2$ receptor subtypes. The phenethylamine or vinylogous phenethylamine compounds of the disclosure are useful in treating diseases, conditions and/or disorders mediated by activity of one or more of the monoamine neurotransmitters.

12 Claims, No Drawings

(56) References Cited

OTHER PUBLICATIONS

Kalix, P., et al., "Differential Effect of Phenylpropyl-and Phenylpentenyl-khatamines on the Release of Radioactivity from Rabbit Atria Prelabelled with 3H-noradrenaline", "Pharm Acta Helv", 1987, pp. 332-334, vol. 62, No. 12.

Parpart, S., et al., "Synthesis of Optically Pure (S)-2-amino-5-arylpent-4-ynoic Acids by Sonogashira Reactions and Their Potential Use as Highly Selective Potent Inhibitors of Aldose Reductase", "RSC Adv.", 2015, pp. 107400-107412, vol. 5.

* cited by examiner

VINYLOGOUS PHENETHYLAMINES AS NEUROTRANSMITTER RELEASERS

This application claims benefit of priority to U.S. Provisional Application No. 62/335,191 filed May 12, 2016. The disclosure of such related provisional application is hereby incorporated herein by reference in its entirety.

GOVERNMENT RIGHTS IN THE INVENTION

This invention was made with government support under Grant No. R01-12970 awarded by the National Institute on Drug Abuse (NIDA), National Institutes of Health. The government has certain rights in the invention.

FIELD

The present disclosure relates to phenethylamine compounds, including vinylogous phenethylamines, useful as monoamine neurotransmitter releasers, methods of using same in a treatment or usage regimen, and pharmaceutical compositions containing such compounds.

In particular, the disclosure is directed to compounds which are monoamine neurotransmitter releasers capable of functioning as dual dopamine and serotonin (DA/5HT) releasers or dopamine releaser and serotonin uptake inhibitor. The disclosure is also directed to pharmaceutical compositions containing one or more dual DA/5HT releaser or dopamine releaser and serotonin uptake inhibitor which may also contain one or more additional therapeutic agents. The disclosure is further directed to methods of treatment of various diseases, conditions and/or disorder that are responsive to administration of dual DA/5HT releasers or a dopamine releaser and serotonin uptake inhibitor, such as substance abuse, depression and other like conditions or neurological diseases.

DESCRIPTION OF THE RELATED ART

Plasma membrane biogenic amine transporters (BATs) regulate neuronal signaling in the central nervous system by transporting previously released monoamine neurotransmitters—dopamine, norepinephrine, and serotonin (DA, NE, and 5-HT transported via DAT (dopamine transporter), NET (norepinephrine transporter), and SERT (serotonin transporter), respectively)—from the synapse back to the neuronal cytoplasm. Ligands that interact with BATs are divided into two general classes: reuptake inhibitors and substrate-type releasers. Both types of ligands elevate extracellular neurotransmitter concentrations but act via different mechanisms. Reuptake inhibitors bind to transporters and block transporter-mediated reuptake of neurotransmitters. Substrate type releasers bind to the substrate site on the transporters, are transported inside the neuron, and promote neurotransmitter efflux by carrier-mediated exchange. Disruption of BAT function plays an important role in the pathophysiology of many neurological diseases such as depression, anxiety, Parkinson's disease, schizophrenia, and psychostimulant addiction.

Psychostimulants, like cocaine and methamphetamine, are addictive drugs that target BATs in the central and peripheral nervous systems to cause a variety of harmful physiological effects in humans. One potential strategy to treat psychostimulant addiction is called agonist substitution therapy whereby patients are administered less potent and less addictive stimulant-like medications. BAT releasers represent one class of compounds being evaluated as potential agonist medications.

Several studies have demonstrated the ability of S(+)-amphetamine,

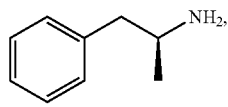

which has a high selectivity for releasing DA relative to 5-HT, to act as an agonist therapy for stimulant dependence. Chronic treatment with S(+)-amphetamine in rhesus monkeys results in a selective dose-dependent decrease in cocaine self-administration compared to food-maintained responding using progressive-ratio, choice, and second-order schedules. In a double-blind, placebo-controlled clinical trial, treatment with S(+)-amphetamine results in a decrease in cocaine use, which is consistent with other clinical trials testing agonist treatments. However, a significant limitation of using S(+)amphetamine as a medication is its abuse potential due to activation of mesolimbic dopamine neurons.

Previous evidence suggests that deficits in both DA and 5-HT are associated with withdrawal symptoms and that elevations in extracellular 5-HT can counteract the stimulant and reinforcing effects of DA (dual deficit model of stimulant addiction). One possible advantage of using dual DA/5-HT releasers as agonist medications is their combined ability to provide the necessary stimulant-like properties required for therapeutic efficacy (i.e., DA release) while reducing abuse liability (5-HT release). As such, multiple lines of evidence show that 5-HT elevations can reduce drug seeking behavior. In vivo studies conducted in rats reveal that 5-HT release decreases the stimulant effects of amphetamine-type drugs and that fenfluramine, for example, (a 5-HT releaser) dose-dependently attenuates cue-reinstated cocaine-seeking behavior. The reduction in drug-seeking behavior observed in rats translates to humans in that fenfluramine significantly reduces cocaine craving in abstinent cocaine-dependent patients. Further, in preliminary clinical trials, co-administration of the anorectics phentermine (a DA releaser) and fenfluramine (Fen-Phen) shows promise in treating cocaine and alcohol dependence thus supporting the idea of using dual DA/5-HT releasers as therapeutics. However, Fen-Phen and other similar neurotransmitter releasers also have activity commonly associated with adverse effects.

There is a need in the art for neurotransmitter releasers and/or uptake inhibitors useful in substance abuse treatment and providing other therapeutic effects with little or no activity at off-targets commonly associated with adverse effects of known compounds effective as neurotransmitter releasers and/or uptake inhibitors.

SUMMARY

The present disclosure relates to compounds useful as neurotransmitter releasers and/or uptake inhibitors. Such compounds and pharmaceutical compositions containing them may have therapeutic benefit in the treatment of obesity, sleep disorders, neurological diseases, depression, anxiety, ADHD, and substance use disorders including stimulant addiction such as cocaine and methamphetamine addiction, and alcohol addiction. The disclosure provides pharmaceutical compositions comprising the compounds and methods of synthesis of such compounds. In addition, the disclosure includes treatment of diseases, conditions and/or disorders responsive to administration of monoamine releasers and/or monoamine uptake inhibitors.

In one aspect, the disclosure provides phenethylamine compounds capable of functioning as monoamine neurotransmitter releasers and/or uptake inhibitors. In some aspects, the compound may function as a dual dopamine/serotonin (DA/5HT) releaser. In other aspects, the compound may function as a releaser of one transporter and a blocker or uptake inhibitor of another. By way of example, in some aspects, the compound may function as a dopamine releaser and a 5HT uptake inhibitor. In addition, the compounds of the disclosure provide therapeutic benefit without substantial adverse effects from activity at the serotonin-2 receptor subtypes.

In another aspect, the disclosure provides phenethylamine compounds according to Formula I:

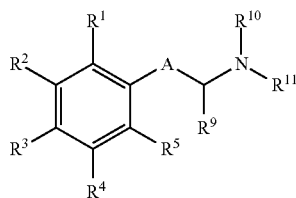

wherein A is $C_{3-4}$ alkynyl or $C_{2-4}$ alkenyl; $R^1$-$R^5$ and $R^9$ are each independently selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or isomer thereof. Preferably, the compounds of Formula I will be capable of functioning as monoamine neurotransmitter releasers and/or monoamine uptake inhibitors.

In another aspect, the disclosure provides vinylogous phenethylamine compounds according to Formula II:

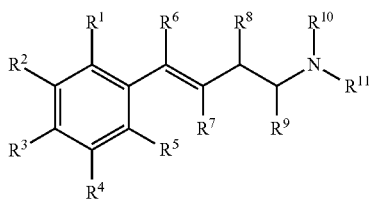

wherein $R^1$-$R^5$ and $R^9$ are each independently selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; $R^6$ and $R^7$ are each independently selected from H or $C_{1-3}$ alkyl; $R^8$ is selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or isomer thereof. Preferably, the compounds of Formula II will be capable of functioning as monoamine neurotransmitter releasers and/or monoamine uptake inhibitors.

In another aspect, the disclosure provides a pharmaceutical composition comprising a phenethylamine compound according to Formula I or II and a pharmaceutically acceptable carrier.

In a further aspect, the disclosure provides a method of treating a disease, condition and/or disorder responsive to activity by monoamine transporter uptake inhibitors and/or monoamine transporter substrate-type releasers comprising administering to a subject in need thereof a therapeutically effective amount of a phenethylamine compound according to Formula I or Formula II. Such methods provide therapeutic benefit to the subject without substantial adverse effects from activity at the serotonin-2 receptor subtypes.

DETAILED DESCRIPTION

As used herein and in the appended claims, the singular forms "a", "and", and "the" include plural referents unless the context clearly dictates otherwise. Like numbers refer to like elements throughout.

The disclosure provides monoamine neurotransmitter uptake inhibitor and/or releaser compounds having biogenic amine transporter activity but lacking substantial activity at $5$-$HT_2$ receptor subtypes.

In one aspect, the disclosure provides phenethylamine compounds according to Formula I:

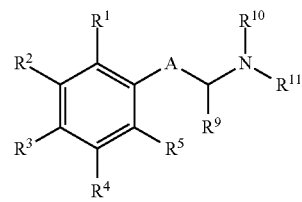

wherein A is $C_{3-4}$ alkynyl or $C_{2-4}$ alkenyl; $R^1$-$R^5$ and $R^9$ are each independently selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or isomer thereof.

In some embodiments, A is $C_{2-4}$ alkenyl. In other embodiments, A is $C_{3-4}$ alkynyl and $R^{10}$ and $R^{11}$ are H. In further embodiments, $R^{10}$ and $R^{11}$ are H and/or at least three of $R^1$-$R^5$ are H. In additional embodiments, at least four of $R^1$-$R^5$ are H. In further embodiments, the alkyl groups are not substituted.

In another aspect, the disclosure provides vinylogous phenethylamine compounds according to Formula II:

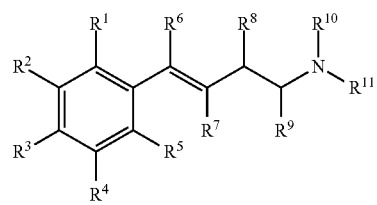

wherein $R^1$-$R^5$ and $R^9$ are each independently selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; $R^6$ and $R^7$ are each independently selected from H or $C_{1-3}$ alkyl; $R^8$ is selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or isomer thereof.

In some embodiments, $R^{10}$ and $R^{11}$ are H and/or at least three of $R^1$-$R^5$ are H. In additional embodiments, at least four of $R^1$-$R^5$ are H. In further embodiments, the alkyl groups are not substituted.

The term "alkyl" as used herein means saturated straight or branched hydrocarbon groups, which may be optionally substituted. In particular embodiments, alkyl refers to groups comprising 1 to 3 carbon atoms ("C1-3 alkyl"). In further embodiments, alkyl refers to groups comprising 1 to 2 carbon atoms ("C1-2 alkyl"), or 2 to 3 carbon atoms ("C2-3 alkyl"). In specific embodiments, alkyl refers to methyl, trifluoromethyl, ethyl, propyl or isopropyl.

In one embodiment, the vinylogous phenethylamine has the structure of formula IIa:

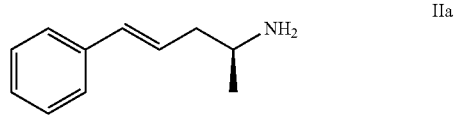

IIa

The term "optionally substituted" refers to moieties optionally containing one or more distinct substituent groups therein that does not preclude the desired pharmaceutical effect, such as, by way of possible example, one or more of the following substituent groups: halo (e.g., Cl, F, Br, and I); halogenated alkyl (e.g., $CF_3$, 2-Br-ethyl, $CH_2F$, $CH_2Cl$, $CH_2CF_3$, or $CF_2$); $CF_3$; hydroxyl; amino; carboxylate; carboxamido; alkylamino; alkoxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 2 to 4 carbon atoms ("C2-4 alkenyl"). In further embodiments, alkenyl refers to groups comprising 2 to 3 carbon atoms ("C2-3 alkenyl"), or 3 to 4 carbon atoms ("C3-4 alkenyl").

The term "alkynyl" as used herein means alkyl moieties wherein at least one saturated C—C bond is replaced by a triple bond. In particular embodiments, alkynyl refers to groups comprising 3 to 4 carbon atoms ("C3-4 alkynyl").

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 3 carbon atoms ("C1-3 alkoxy").

The term "halo" or "halogen" as used herein means fluorine, chlorine, bromine, or iodine.

The term "alkylthio" as used herein means a thio group with one or more alkyl substituents, where alkyl is defined as above.

The term "amino" as used herein means a moiety represented by the structure $NR_2$, and includes primary amines, and secondary and tertiary amines substituted by alkyl (i.e., alkylamino). Thus, $R_2$ may represent two hydrogen atoms, two alkyl moieties, or one hydrogen atom and one alkyl moiety.

The term "derivative" as used herein means a compound that is formed from a similar, beginning compound by attaching another molecule or atom to the beginning compound. Further, derivatives, according to the disclosure, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the disclosure.

The term "active metabolite" as used herein means a physiologically active compound which results from the metabolism of a compound of the disclosure, or a prodrug thereof, when such compound or prodrug is administered to a mammal.

The compounds of the disclosure may be included in pharmaceutical compositions comprising a phenethylamine compound according to Formula I or Formula II and a pharmaceutically acceptable carrier. Such pharmaceutical compositions may be useful in the treatment or alleviation of diseases, conditions or disorders responsive to administration of monoamine releasers and/or monoamine uptake inhibitors without causing substantial undesirable effects. Such diseases, conditions or disorders may include obesity, sleep disorders, neurological diseases, depression, anxiety, ADHD, and substance use disorders including psychostimulant addiction such as cocaine and methamphetamine addiction, and alcohol addiction.

The term "psychostimulant" refers to a broadly defined class of compounds or drugs that stimulate the central and peripheral nervous systems, producing a spectrum of effects in humans, including cardiovascular stimulation, mood elevation and a decreased need for sleep. At higher doses, or after longer periods of use, psychostimulants can cause a range of disordered thought processes, including severe psychotic episodes. Examples of psychostimulants include cocaine, methamphetamine, methylphenidate, amphetamine, substituted amphetamine, phentermine, diethylpropion, phendimetrazine, benzphetamine, and 3,4-methylenedioxymethamphetamine.

The term "dual dopamine/serotonin (DA/5HT) releaser" refers to compounds capable of functioning as at least a partial substrate-type releaser for both dopamine and serotonin. Substrate type releasers bind to the substrate site on the transporters, e.g., the dopamine and serotonin transporters, are transported inside the neuron, and promote neurotransmitter efflux by carrier-mediated exchange. Such dual dopamine/serotonin (DA/5HT) releaser compounds may be capable of providing therapeutic effects of stimulant-type releasers while being minimally reinforcing since dopamine release provides a stimulant-like property believed to be required for therapeutic efficacy and 5HT release is believed to reduce abuse liability. Dual dopamine/serotonin (DA/5HT) releaser compounds may be active in both uptake inhibition and release assays.

The term "reuptake inhibitors" refers to compounds that bind to transporters and block transporter-mediated reuptake of monoamine neurotransmitters.

The term "monoamine" as used herein encompasses monoamine neurotransmitters and neuromodulators. In particular, it is used to refer to dopamine, norepinephrine, and serotonin. Monoamine transporters facilitate the reuptake or reabsorption of these monoamines into the presynapses of an individual.

The terms "therapeutically effective amount" or "therapeutically effective dose" as used herein are interchangeable and mean a concentration of a compound according to the disclosure, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The disclosure provides pharmaceutical compositions comprising a pharmaceutically acceptable carrier and a phenethylamine according to Formula I:

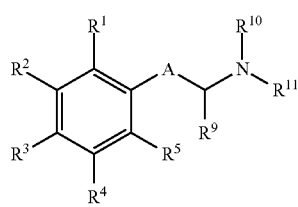

wherein A is $C_{3-4}$ alkynyl or $C_{2-4}$ alkenyl; $R^1$-$R^5$ and $R^9$ are each independently selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or isomer thereof.

The disclosure further provides pharmaceutical compositions comprising a pharmaceutically acceptable carrier and a vinylogous phenethylamine according to Formula II:

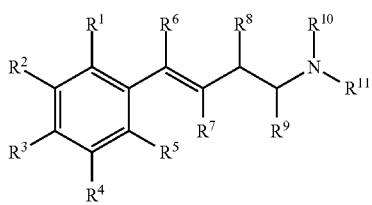

wherein $R^1$-$R^5$ and $R^9$ are each independently selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; $R^6$ and $R^7$ are each independently selected from H or $C_{1-3}$ alkyl; $R^8$ is selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or isomer thereof.

Compounds according to Formula I and Formula II preferably are capable of functioning as dual dopamine/serotonin (DA/5HT) releasers or as a dopamine releaser and a 5HT uptake inhibitor. The compounds of the disclosure are useful in methods for treating or delaying the progression of disease, condition and/or disorder that is alleviated by inhibiting monoamine reuptake in a patient or by selectively binding one or more monoamine transporters.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition.

As used herein, the term "subject" refers to a human or any non-human animal (e.g., mouse, rat, rabbit, dog, cat, cattle, swine, sheep, horse or primate). In many embodiments, a subject is a human being. A subject can be a patient, which refers to a human presenting to a medical provider for diagnosis or treatment of a disease, condition and/or disorder. The term "subject" is used herein interchangeably with "individual" or "patient." A subject can be afflicted with or is susceptible to a disease, condition or disorder but may or may not display symptoms of the disease, condition or disorder.

The disclosure specifically provides a method of treating a disease, condition or disorder responsive to monoamine transporter uptake inhibitors and/or monoamine transporter substrate-type releasers comprising administering to a subject in need thereof a therapeutically effective amount of a phenethylamine compound according to Formula I or Formula II or a pharmaceutically acceptable ester, amide, salt, solvate, prodrug, or isomer thereof.

The compounds of the disclosure avoid the side effects exhibited after administration of previously known monoamine transporter uptake inhibitors and/or monoamine transporter substrate-type releasers due to lack of substantial agonist activity at the 5HT receptors, particularly, at the $5HT_{2b}$ and $5HT_{2a}$ receptors. This lack of substantial activity at "off-targets" allows for reduced or attenuated adverse effects from the administration of the monoamine transporter uptake inhibitors and/or monoamine transporter substrate-type releasers disclosed herein to subjects in need of treatment for diseases, conditions and/or disorders capable of modulation by activity at the biogenic amine transporters.

The disease, condition and/or disorder to be treated with the phenethylamines of the disclosure may include obesity, sleep disorders, neurological diseases, depression, anxiety, ADHD, and substance use disorders including stimulant addiction such as cocaine and methamphetamine addiction, and alcohol addiction. In embodiments, the condition or disorder is stimulant addiction, more particularly, psychostimulant addiction.

In one aspect of the disclosure, methods of treating psychostimulant addiction are provided comprising administering to a subject in need thereof a therapeutically effective amount of a compound according to the structure of Formula I:

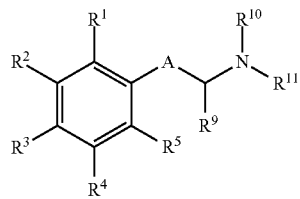

wherein A is $C_{3-4}$ alkynyl or $C_{2-4}$ alkenyl; $R^1$-$R^5$ and $R^9$ are each independently selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or isomer thereof.

In another aspect of the disclosure, methods of treating psychostimulant addiction are provided comprising administering to a subject in need thereof a therapeutically effective amount of a compound according to the structure of Formula II:

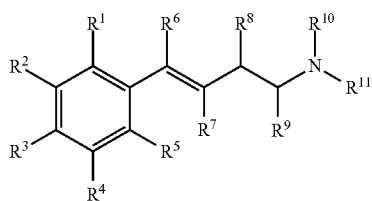

wherein $R^6$ and IC are each independently selected from H or $C_{1-3}$ alkyl and $R^8$ is selected from H, OH, optionally substituted $C_{1-3}$ alkyl, optionally substituted $C_{1-2}$ alkoxy, optionally substituted $C_{2-3}$ alkenyl, optionally substituted $C_{2-3}$ alkynyl, halo, amino, CN, $CF_3$, and $NO_2$; or a pharmaceutically acceptable ester, amide, salt, solvate, prodrug, or isomer thereof.

The phenethylamine compounds disclosed herein as active agents may contain chiral centers, which may be either of the (R) or (S) configuration, or may comprise a mixture thereof. Accordingly, the present disclosure also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds disclosed herein. Isomers may include geometric isomers. Examples of geometric isomers include, but are not limited to, cis isomers or trans isomers across a double bond. Other isomers are contemplated among the compounds of the present disclosure. The isomers may be used either in pure form or in admixture with other isomers of the compounds described herein.

Various methods are known in the art for preparing optically active forms and determining activity. Such methods include standard tests described herein and other similar tests which are well known in the art. Examples of methods that can be used to obtain optical isomers of the compounds according to the present disclosure include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular to the extent of 60% or more, 75% or more, 90% or more, 95% or more, or 98% or more, including 100%.

The compounds of the present disclosure may be utilized per se or in the form of a pharmaceutically acceptable ester, amide, salt, solvate, prodrug, or isomer. For example, the compound may be provided as a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this disclosure.

Such pharmacologically and pharmaceutically acceptable salts can be prepared by reaction of the drug with an organic or inorganic acid, using standard methods detailed in the literature. Examples of pharmaceutically acceptable salts of the compounds useful according to the disclosure include acid addition salts. Salts of non-pharmaceutically acceptable acids, however, may be useful, for example, in the preparation and purification of the compounds. Suitable acid addition salts according to the present disclosure include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

While it is possible for the compounds of the present disclosure to be administered in the raw chemical form, it is preferred for the compounds to be delivered as a pharmaceutical formulation. Accordingly, there are provided by the present disclosure pharmaceutical compositions comprising at least one compound capable of functioning as a dual DA/5-HT releaser or a DA releaser and a 5HT reuptake inhibitor. As such, the formulations of the present disclosure comprise a compound of Formula I or a compound of Formula II, as described above, or a pharmaceutically acceptable ester, amide, salt, or solvate thereof, together with one or more pharmaceutically acceptable carriers therefore, and optionally, other therapeutic ingredients.

By "pharmaceutically acceptable carrier" is intended a carrier that is conventionally used in the art to facilitate the storage, administration, and/or the healing effect of the agent. The carrier(s) must be pharmaceutically acceptable in the sense of being compatible with the other ingredients of the formulation and not unduly deleterious to the recipient thereof. A carrier may also reduce any undesirable side effects of the agent. Such carriers are known in the art.

Adjuvants or accessory ingredients for use in the formulations of the present disclosure can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the disclosure are listed in "Remington: The Science & Practice of Pharmacy," 19th ed., Williams & Williams, (1995), in the "Physician's Desk Reference," 52nd ed., Medical Economics, Montvale, N.J. (1998), and in "Handbook of Pharmaceutical Excipients," Third Ed., Ed. A. H. Kibbe, Pharmaceutical Press, 2000.

Pharmaceutical formulations according to the present disclosure are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds of Formula I or Formula II according to the present disclosure (or a pharmaceutically acceptable ester, amide, salt, or solvate thereof) with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations according to the present disclosure suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present disclosure.

A tablet containing a compound according to the present disclosure may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like.

Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present disclosure may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for patenteral administration may be presented in unit-dose or multi-dose containers, such as, for example, sealed ampoules and viles, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present disclosure may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Formulations for rectal delivery of the compounds of the present disclosure include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about six hours.

The compounds of Formula I or Formula II above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy.

The methods of formulation typically include the step of bringing a compound of Formula I of Formula II into association with a carrier that constitutes one or more accessory ingredients. In general, the compositions are prepared by bringing a compound of the disclosure into association with a liquid carrier to form a solution or a suspension, or alternatively, bringing a compound of the disclosure into association with formulation components suitable for forming a solid, optionally a particulate product, and then, if warranted, shaping the product into a desired delivery form. Solid formulations of the disclosure, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound of Formula I or Formula II in the formulation will vary depending the specific compound selected, dosage form, target patient population, and other considerations, and will be readily determined by one skilled in the art.

The amount of the compound of Formula I or Formula II in the formulation will be that amount necessary to deliver a therapeutically effective amount of the compound to a patient in need thereof to achieve at least one of the therapeutic effects associated with the compounds of the disclosure. In practice, this will vary widely depending upon the particular compound, its activity, the severity of the condition to be treated, the patient population, the stability of the formulation, and the like.

The methods of treatment according to the disclosure generally include administration of a therapeutically effective amount of a compound of Formula I or Formula II, optionally in a pharmaceutical composition including one or more pharmaceutically acceptable carriers, wherein the therapeutically effective amount is preferably sufficient to effect release of dopamine and serotonin or effect release of dopamine and inhibition of uptake of serotonin. The therapeutically effective amount is further preferably sufficient to provide relief to the patient in the symptoms of the disease, condition or disorder for which the patient is being treated.

Compositions will generally contain anywhere from about 1% by weight to about 99% by weight of a compound of the disclosure, typically from about 5% to about 70% by weight, and more typically from about 10% to about 50% by weight, and will also depend upon the relative amounts of excipients/additives contained in the composition.

In specific embodiments, the compounds of Formulas I or II, or a pharmaceutically acceptable ester, amide, salt, solvate, prodrug, or isomer thereof, may be used in combination with other biologically active agents typically recognized as useful for treating the diseases, conditions and/or disorders discussed herein. Such biologically active agents for use in combination with the phenethylamine compounds of the disclosure may include, by way of example, antidepressants such as selective serotonin reuptake inhibitors (SSRIs), tricyclics, serotonin norepinephrine reuptake inhibitors and norepinephrine and dopamine reuptake inhibitors (NDRIs), monoamine oxidase inhibitors (MAOIs), mood stabilizers, antinarcoleptics, or antipsychotics.

EXAMPLES

The present disclosure also encompasses methods of preparing compounds with structures as disclosed herein. To obtain compounds effective as dual DA and 5-HT releasers, information available regarding 1-naphthyl-2-aminopropane (PAL-287 (PAL, Phenyl Amine Library)), as a comparative compound, was evaluated. PAL-287,

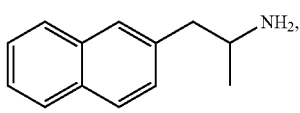

releases radiolabeled neurotransmitters from DAT, SERT, and NET with $EC_{50}$ values of 12.6 nM, 3.4 nM, and 11.1 nM, respectively (Table 1). In vivo microdialysis experiments in rats corroborate the in vitro data by showing that PAL-287 (1-3 mg/kg I.v.) increases extracellular DA and 5-HT in the frontal cortex, with effects on 5-HT being larger (464% increase compared to 133% increase). Furthermore, in rats, PAL-287 causes significantly less motor stimulation compared to S(+)-amphetamine, which has 71-fold greater potency to release DA compared to 5-HT; importantly high doses of PAL-287 do not cause depletion of cortical 5-HT. In rhesus monkeys trained to self-administer cocaine, PAL-287 produces a dose-dependent decrease in cocaine self-administration and significantly decreases cocaine-versus food-maintained responding at 1.0 mg/kg/h. Overall, the data collected with the non-amphetamine analog, PAL-287, support the hypothesis that dual DA/5-HT releasers possess the therapeutic effects of amphetamine-type releasers while being minimally reinforcing.

Accordingly, a series of phenethylamines were synthesized and evaluated for transporter activity. Four groups of phenethylamine analogs were synthesized as shown below.

Group I

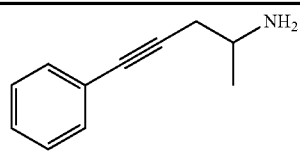

4

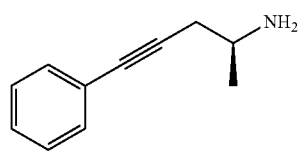

S-4

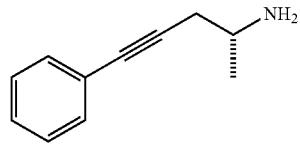

R-4

Group II

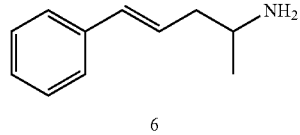

6

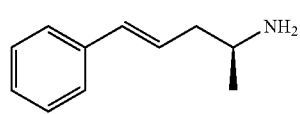

S-6

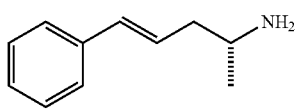

R-6

Group III

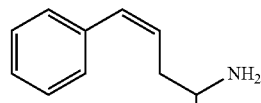

8

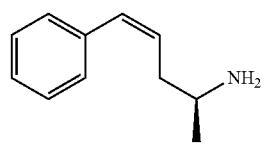

S-8

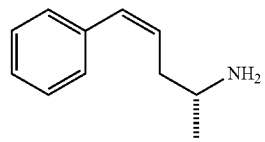

R-8

Group IV

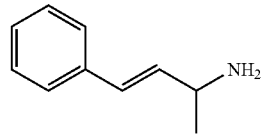

10

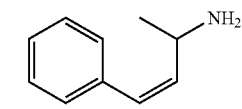

11

Group I consisted of the racemic alkynyl isostere 4, as well as the two chiral isosteres, S-4 and R-4. Group II consisted of the racemic and chiral (E)-alkenyl isosteres (6, S-6, R-6), while group III consisted of the corresponding (Z)-alkenyl isosteres (8, S-8, R-8). The analogs of group IV (10, 11) have one less carbon between the phenyl ring and the amine group. All analogs were synthesized in three or four steps from commercially available materials. Scheme 1 shows the synthesis of the (S)-stereoisomers from groups I-III.

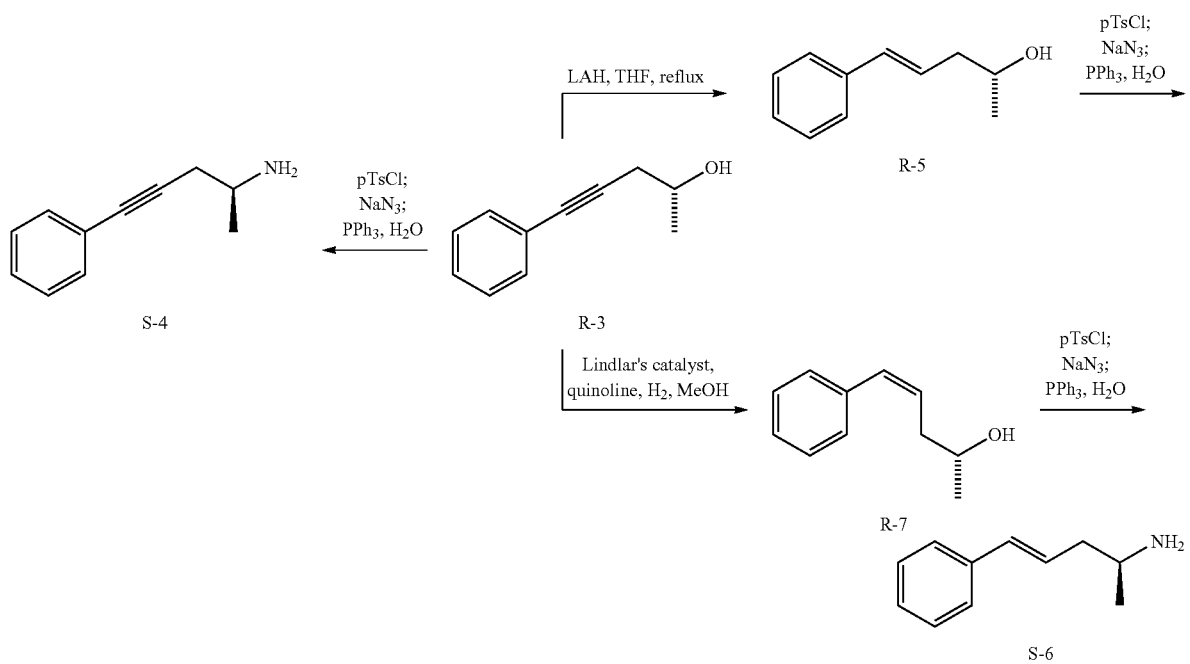

To synthesize group I, alkyne S-4, commercially available alcohol R-3 was converted to the tosylate, which underwent displacement with inversion of configuration to the azide, which was reduced under the Staudinger conditions to provide S-4. The same commercially available starting alcohol R-3 was selectively reduced with Lithium Aluminum Hydride (LAH) or Lindlar's catalyst to afford the corresponding (E)- or (Z)-olefins, R-5 and R-7, respectively. These olefins were then converted to amines S-6 and S-8, respectively, using the same three step tosylation/azide formation/Staudinger reduction steps. The (R)stereoisomers and the racemates for groups I-III were synthesized using the same pathway starting with the corresponding commercially available (S)-alcohol and racemic alcohol, respectively.

Scheme 2 shows the synthesis of group IV vinylogous phenethylamines (10, 11) from commercially available alcohol 9 using the same pathway as the compounds synthesized in Scheme 1, except that mesylation was performed instead of tosylation due to stability issues.

Scheme 2: Synthesis of group IV analogs

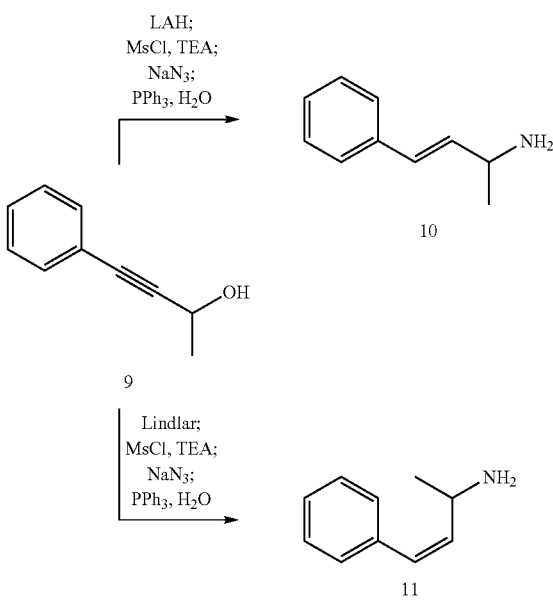

BAT activity was measured using synaptosomes prepared from rat brain homogenates according to the protocol developed by Rothman and co-workers (Rothman, et al., *Eur. J. Pharmacol.* 2002, 447(1), 51). Compounds were first screened in uptake inhibition and release assays to determine the exact mode of drug action. Compounds active in both assays are releasers while compounds active only in the uptake inhibition assay are uptake inhibitors. Active compounds were then fully characterized by running 8-point concentration response curves in the assay corresponding to their mechanism of action. Substrate reversal experiments were conducted to validate substrate activity. The analogs were also tested for agonist activity at the serotonin-2 receptor subtypes (5-HT$_{2A}$, 5-HT$_{2B}$, 5-HT$_{2C}$) using in vitro calcium mobilization assays in transfected HEK293 cells as previously described. These receptors are associated with the pharmacology of abused drugs, as 5-HT$_{2A}$ agonists are thought to be hallucinogenic while 5-HT agonists are associated with valvular heart disease and pulmonary hypertension; activity at these receptors would be considered off-target liabilities. On the other hand, agonists at 5-HT$_{2C}$ may be beneficial as potential pharmacotherapies for drug abuse and appetite suppression.

Table 1 shows the transporter data for the analogs. All compounds were active as DAT and NET releasers with varying potencies and all but two compounds, 10 and 11, were active as SERT releasers. At the DAT, group I alkynes had similar potencies with S-4 being the most potent with an EC$_{50}$ value of 443 nM. At the SERT, the alkynes also had similar potencies with R-4 being the most potent with an EC$_{50}$ value of 288 nM. At the NET, alkyne R-4 was the most potent (EC$_{50}$=496 nM) and 4 was the least potent (EC$_{50}$=2980 nM). The group II (E)-alkenes were potent at all three transporters, with EC$_{50}$ values less than 540 nM. At the DAT, group II (E)-alkenes had similar potencies with R-6 being the least potent (EC$_{50}$=540 nM) and S-6 being the most potent with an EC$_{50}$ value of 206 nM.

At the SERT and NET, S-6 was the most active compound in this group with EC$_{50}$ values of 40 nM and 138 nM, respectively. At the DAT, group III (Z)-alkenes were less than 1500 nM, with S-8 being the most potent at 304 nM. At the SERT, analogs 8 and S-8 had similar potencies with 8 being slightly more potent (EC$_{50}$=646 nM). At the NET, S-8 was the most potent analog with an EC$_{50}$ value of 170 nM. Group IV analogs were inactive at SERT and relatively weak releasers at DAT with 10 being the most potent (EC$_{50}$=666 nM). However, both analogs had similar potencies at the NET (EC$_{50}$≈300 nM).

TABLE 1

Structure-Activity of a Series of Vinylogous Amphetamine Analogs for Releasing Radiolabeled Substrates from DAT, SERT and NET

| PAL # | Group | DAT EC$_{50}$, (nM ± SD)[a] | SERT EC$_{50}$, (nM ± SD)[a] | NET EC$_{50}$, (nM ± SD)[a] | 5-HT$_{2A}$[b] EC$_{50}$, (nM ± SEM) | 5-HT$_{2B}$[b] EC$_{50}$, (nM ± SEM) | 5-HT$_{2C}$[b] EC$_{50}$, (nM ± SEM) |
|---|---|---|---|---|---|---|---|
| (+)-AMP | 1 | | 24.8 ± 3.5 | 1770 ± 94 | 7.1 ± 1 | IA | IA | IA |
| 287 | 2 | | 12.6 ± 0.4 | 3.4 ± 0.2 | 11.1 ± 0.9 | 466 nM[c] | 40 nM[c] | 2.3 nM (20%)[c] |
| 869 | 4 | I | 997 ± 220 | 384 ± 110 | 2980 ± 490 | >10k | IA | IA |
| 870 | S-4 | I | 443 ± 100 | 756 ± 79 | 784 ± 190 | 4950 ± 1400 | IA | IA |
| 871 | R-4 | I | 660 ± 190 | 288 ± 84 | 496 ± 160 | >10k | IA | IA |
| 872 | 6 | II | 272 ± 44 | 54 ± 8 | 239 ± 59 | 5620 ± 1700 | IA | IA |
| 875 | S-6 | II | 206 ± 26 | 40 ± 9 | 138 ± 260 | IA | IA | IA |
| 873 | R-6 | II | 540 ± 87 | 109 ± 29 | 279 ± 24 | >10k | IA | IA |
| 904 | 8 | III | 900 ± 100 | 646 ± 70 | 621 ± 190 | 1860 ± 76 | IA | >10k |
| 905 | S-8 | III | 304 ± 100 | 863 ± 86 | 170 ± 32 | 1600 ± 320 | IA | >10k |
| 906 | R-8 | III | 1416 ± 180 | 1156 ± 160 | 211 ± 42 | >10000 | IA | IA |
| 881 | 10 | IV | 666 ± 160 | >10k | 308 ± 100 | IA | IA | IA |
| 893 | 11 | IV | 1114 ± 150 | >10k | 301 ± 76 | IA | IA | IA |

In Table 1, a: EC$_{50}$ values were determined as described below, each value is mean±SD (n=3); b: Calcium mobilization EC$_{50}$ values were determined as described below; c: data is from Rothman, R B.; Blough, B. E.; Baumann, M. H. Trends Pharmacol. Sci. 2006, 27(12), 612; IA=inactive at 10 µM.

From a structure-activity perspective, all compounds were substrates for the transporters, indicating that the transporters can translocate larger structures than previously believed. All compounds, except group IV, were dual DA/5-HT releasers, but with varying degrees of transporter selectivity. The group I alkynes did not exhibit much selectivity for releasing 5-HT compared to DA as the racemic analog 4 and R-4 were only 2.6-fold and 2.3-fold, respectively, more potent at the DAT. The S-4 was essentially equipotent at the DAT and SERT. The group II alkenes were all more selective at SERT relative to DAT with 5-fold greater potency at SERT. This group was interesting because the activities at the transporters were all very similar, indicating no differences between chiral isomers, R-6 and S-6, and the racemate 6. The group III (Z)-olefins were similar to the group I alkynes as the analogs did not show much SERT/DAT selectivity. The racemic analog 8 and R-8 had similar potencies for releasing 5-HT relative to DA (1.4- and 1.2-fold, respectively) while 5-8 was slightly more potent for releasing DA relative to 5-HT (2.2-fold). Removing a carbon between the alkene and the amine (group IV) resulted in analogs that were selective at DAT and NET. These compounds were inactive at SERT indicating they could not bind to the site of translocation; this activity profile suggests the compounds may be weak stimulants.

It has been found in some studies that NE release almost always parallels DA release with slightly higher potency. While most of the vinylogous analogs follow the DA/NE release trend, a few compounds show selectivity for DAT or NET. Group I racemic alkyne 4 was 3-fold more potent at releasing DA compared to NE with EC$_{50}$ values of 997 nM and 2980 nM, respectively. Analog S-4 followed the typical trend at DAT and NET with $EC_{50}$ values of 660 nM and 496 nM, respectively, while activity at DAT and NET for analog R-4 was reversed with $EC_{50}$ values of 443 nM and 784 nM, respectively. All group II (E)-alkenes and two group III (Z)-alkenes followed the typical trend; however, group III (Z)-alkene R-8 was 6.7-fold selective for releasing NE relative to DA with $EC_{50}$ values of 211 nM and 1416 nM, respectively. Both group IV analogs, 10 and 11, were more potent at NET compared to DAT, but with different selectivities (2.2-fold and 3.7-fold, respectively).

Group II (E)-alkenes were the most active compounds compared to the other three groups. The most potent analog at the DAT, SERT, and NET was (E)-alkene 5-6 with $EC_{50}$ values of 206 nM, 40 nM, and 138 nM, respectively. This analog retains the same configuration as S(+)-amphetamine, has the same number of carbons between the phenyl and amine groups as PAL-287, and has a similar steric conformation as PAL-287, compared to the more sterically hindered (Z)-olefins. While PAL-287 is 10-fold more potent than S-6 at all three transporters, the compounds share some activity characteristics. S-6 has 5-fold 5-HT/DA release potency, similar to comparative compound PAL-287, which has 3.7-fold selectivity. S-6 has 3.5-fold higher potency for 5-HT release compared to NE release, which is similar to PAL-287's 3.3-fold selectivity, and both compounds have almost equal DA/NE release potencies.

The vinylogous analogs of the disclosure were also evaluated for agonist activity at $5\text{-HT}_{2A}$, $5\text{-HT}_{2B}$, and $5\text{-HT}_{2C}$ receptors using in vitro calcium mobilization assays (Table 1). Overall, the analogs had varying degrees of weak activity at all three receptors, making them much more like S(+)-amphetamine (inactive in all three assays) than PAL-287 (Table 1). Previous functional studies reveal that PAL-287 is a full agonist at $5\text{-HT}_{2A}$ and $5\text{-HT}_{2B}$ receptors ($EC_{50}$=466 nM and 40 nM, respectively) and a partial agonist ($EC_{50}$=2.3 nM, $E_{MAX}$=20%) at $5\text{-HT}_{2C}$. At $5\text{-HT}_{2A}$, the vinylogous analogs were all less potent than PAL-287 as most of them were inactive (S-6, 10, 11) or had $EC_{50}$ values >10 μM (4, R-4, R-6, R-8). The remaining analogs had potencies in the micromolar range. Analog S-8, which had an $EC_{50}$ value of 1600 nM and $E_{MAX}$ of 102%, was the most potent and efficacious analog. The racemic analog 8 had a similar potency ($EC_{50}$=1860 nM) and efficacy ($E_{MAX}$=90%). The only other compounds that were active were alkyne S-4 and racemic alkene 6, which had a 2.7-fold and 3-fold reduction in potency, respectively, compared to 8. These compounds were also not as efficacious and had $E_{MAX}$ values in the lower 80% range. At $5\text{-HT}_{2B}$, all the analogs were inactive. This was interesting because PAL-287 was active at $5\text{-HT}_{2B}$ as an agonist with an $EC_{50}$ value of 40 nM. At $5\text{-HT}_{2C}$, only group III (Z)-alkenes 8 and S-8 were weak agonists with activity less than 50% of the control 5-HT $E_{MAX}$ at 10 μM. The most active transporter compound (S-6) was inactive at all three receptors, indicating that this compound may not produce the typical effects associated with agonist activity at the 5-HT2 receptors. Analog S-6 was also inactive in in vitro $5\text{-HT}_2$ calcium mobilization assays, indicating no potential in vivo effects.

The experimental synthesis and activity investigations are set forth in detail below.

Example 1

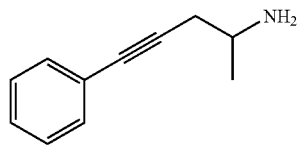

1-Methyl-4-phenyl-but-3-ynylamine (4)

To a stirring solution of known alcohol R-3 (432 mg, 2.70 mmol) in pyridine (1.7 mL) at 0° C. under $N_2$ was slowly added p-toluenesulfonyl chloride (1.03 g, 5.40 mmol) in pyridine (1 mL). The reaction mixture was allowed to warm to room temperature slowly and then stirred overnight. The reaction mixture was poured into an Erlenmeyer flask containing ice and 10% aqueous HCl, using $CH_2Cl_2$ to aid in the transfer, and stirred until it reached room temperature. The biphasic mixture was partitioned in a separatory funnel. The aqueous layer was extracted twice with $CH_2Cl_2$ and the combined organic extracts were washed three times with 10% aqueous HCl, once with water, and once with brine, dried over $Na_2SO_4$, and filtered. Concentration under reduced pressure afforded the crude tosylate as a brown oil contaminated with some unreacted starting material.

To a stirring solution of the crude tosylate (849 mg, 2.70 mmol) in DMF (9 mL) was added $NaN_3$ (702 mg, 10.8 mmol) and the suspension was allowed to stir vigorously overnight. The reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded 258 mg (52% yield) of the azide as a clear oil.

To a stirring solution of the azide (158 mg, 0.853 mmol) in THF under $N_2$ (4.5 mL) was added $PPh_3$ (449 mg, 1.71 mmol). Water (0.53 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 10% $MeOH/CH_2Cl_2$ to 20% $MeOH/CH_2Cl_2$ gradient) afforded 114 mg (84% yield) of amine 4 as a pale yellow oil. $^1H$ NMR ($CDCl_3$, 300 MHz) δ 7.42-7.39 (m, 2H), 7.29-7.27 (m, 3H), 3.24-3.14 (m, 1H), 2.56-2.37 (qd mixed with br. s, 4H), 1.21 (d, J=6.0 Hz, 3H); $^{13}C$ NMR ($CDCl_3$, 75 MHz) ppm 131.6, 128.2, 127.8, 123.6, 87.1, 82.7, 46.4, 30.3, 22.7; MS (APCI) $(M+1)^+$ 160.2, found 160.1. The hydrochloride salt had mp 131-132° C.; Anal. ($C_{11}H_{14}ClN$) C, H, N.

Example 2

(1S)-1-Methyl-4-phenyl-but-3-ynylamine (S-4)

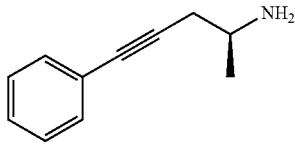

To a stirring solution of known alcohol R-3 (580 mg, 3.62 mmol) in pyridine (2 mL) at 0° C. under N₂ was slowly added p-toluenesulfonyl chloride (1.38 g, 7.24 mmol) in pyridine (1.6 mL). The reaction mixture was allowed to warm to room temperature slowly and then stirred overnight. The reaction mixture was poured into an Erlenmeyer flask containing ice and 10% aqueous HCl, using $CH_2Cl_2$ to aid in the transfer, and stirred until it reached room temperature. The biphasic mixture was partitioned in a separatory funnel. The aqueous layer was extracted twice with $CH_2Cl_2$ and the combined organic extracts were washed three times with 10% aqueous HCl, once with water and once with brine, dried over $Na_2SO_4$, and filtered. Concentration under reduced pressure afforded 949 mg (83% yield) of the crude tosylate as a white solid.

To a stirring solution of the crude tosylate (949 mg, 3.02 mmol) in DMF (10 mL) was added $NaN_3$ (787 mg, 12.1 mmol) and the suspension was allowed to stir vigorously overnight. The reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded 490 mg (88% yield) of the azide as a clear oil.

To a stirring solution of the azide (490 mg, 2.65 mmol) in THF (14 mL) under $N_2$ was added $PPh_3$ (1.39 g, 5.30 mmol). Water (1.7 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 10% $MeOH/CH_2Cl_2$ to 20% $MeOH/CH_2Cl_2$ gradient) afforded 261 mg (62% yield) of amine S-4 as a pale yellow oil. $[\alpha]^{20}_D$ +11.4 g/mL (c 0.0007, MeOH); ¹H NMR ($CD_3OD$, 300 MHz) δ 7.40-7.36 (m, 2H), 7.31-7.28 (m, 3H), 3.14-3.05 (m, 1H), 2.48-2.46 (m, 2H), 1.21 (d, J=6.0 Hz, 3H); ¹³C NMR ($CDCl_3$, 75 MHz) ppm 131.6, 128.2, 127.7, 123.7, 87.3, 82.6, 46.4, 30.7, 23.0; MS (APCI) (M+1)⁺ 160.2, found 160.1. The hydrochloride salt had mp 141-142° C.; Anal. ($C_{11}H_{14}ClN\cdot0.2H_2O$) C, H, N.

Example 3

(1R)-1-Methyl-4-phenyl-but-3-ynylamine (R-4)

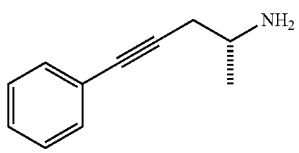

To a stirring solution of known alcohol S-3 (560 mg, 3.50 mmol) in pyridine (2 mL) at 0° C. under $N_2$ was slowly added p-toluenesulfonyl chloride (1.33 g, 7.00 mmol) in pyridine (1.5 mL). The reaction mixture was allowed to warm to room temperature slowly and then stirred overnight. The reaction mixture was poured into an Erlenmeyer flask containing ice and 10% aqueous HCl, using $CH_2Cl_2$ to aid in the transfer, and stirred until it reached room temperature. The biphasic mixture was partitioned in a separatory funnel. The aqueous layer was extracted twice with $CH_2Cl_2$ and the combined organic extracts were washed three times with 10% aqueous HCl, once with water and once with brine, dried over $Na_2SO_4$, and filtered. Concentration under reduced pressure afforded the crude tosylate as a brown oil contaminated with some unreacted starting material.

To a stirring solution of the crude tosylate in DMF (11 mL) was added $NaN_3$ (826 mg, 12.7 mmol) and the suspension was allowed to stir vigorously overnight. The reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded 370 mg (63% yield) of the azide as a clear oil.

To a stirring solution of the azide (370 mg, 2.00 mmol) in THF (11 mL) under $N_2$ was added $PPh_3$ (1.05 g, 4.00 mmol). Water (1.3 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 10% $MeOH/CH_2Cl_2$ to 20% $MeOH/CH_2Cl_2$ gradient) afforded 213 mg (67% yield) of amine R-4 as a pale yellow oil. $[\alpha]^{20}_D$ −4.2 g/mL (c 0.0050, MeOH); ¹H NMR ($CDCl_3$, 300 MHz) δ 7.43-7.40 (m, 2H), 7.29-7.27 (m, 3H), 3.24-3.14 (m, 1H), 2.44 (qd, J=54.0, 42.0, 24.0, 6.0 Hz, 2H), 1.81 (br. s, 2H), 1.22 (d, J=6.0 Hz, 3H); ¹³C NMR ($CDCl_3$, 75 MHz) ppm 131.6, 128.2, 127.7, 123.7, 87.3, 82.6, 46.5, 30.6, 23.0; MS (APCI) (M+1)⁺ 160.2, found 160.0. The hydrochloride salt had mp 143-144° C.; Anal. ($C_{11}H_{14}ClN$) C, H, N.

Example 4

(3E)-1-Methyl-4-phenyl-but-3-enylamine (6)

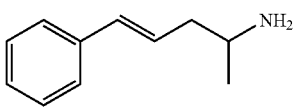

To a stirring solution of LAH (12.5 mL, 1M in THF, 12.5 mmol) in dry THF (15 mL) at 0° C. under $N_2$ was slowly added alcohol 3a (500 mg, 3.12 mmol) in dry THF (3 mL). CAUTION: Bubbling results due to $H_2$ gas evolution. After the bubbling ceased, the reaction mixture was slowly warmed to room temperature and then refluxed for 5 h. After cooling to room temperature, then to 0° C., the reaction mixture was carefully quenched with the successive addition of 0.47 mL H$_2$O, 0.47 mL 3 M aqueous HCl, 1.4 mL H$_2$O, and 1.4 mL 3 M aqueous HCl. CAUTION: Vigorous exotherm and bubbling results due to H$_2$ gas evolution. After the bubbling ceased, the quenched reaction mixture was slowly warmed to room temperature, stirred for 30 min, and transferred to a separatory funnel. The aqueous layer was extracted twice with ether and the combined organic extracts were washed with saturated aqueous NaHCO$_3$, water, and brine, dried over Na$_2$SO$_4$, and filtered. Concentration under reduced pressure afforded 446 mg (88% yield) of the crude (E)-olefin 5 as a clear oil.

To a stirring solution of the (E)-olefin 5 (738 mg, 4.55 mmol) in pyridine (3 mL) at 0° C. under N$_2$ was slowly added p-toluenesulfonyl chloride (1.73 g, 9.10 mmol) in pyridine (1.6 mL). The reaction mixture was allowed to warm to room temperature slowly and then stirred overnight. The reaction mixture was poured into an Erlenmeyer flask containing ice and 10% aqueous HCl, using CH$_2$Cl$_2$ to aid in the transfer, and stirred until it reached room temperature. The biphasic mixture was partitioned in a separatory funnel. The aqueous layer was extracted twice with CH$_2$Cl$_2$ and the combined organic extracts were washed three times with 10% aqueous HCl, once with water and once with brine, dried over Na$_2$SO$_4$, and filtered. Concentration under reduced pressure afforded the crude tosylate as a brown oil contaminated with some unreacted starting material.

To a stirring solution of the crude tosylate in DMF (15 mL) was added NaN$_3$ (1.18 g, 18.2 mmol) and the suspension was allowed to stir vigorously overnight. The reaction mixture was poured onto water and ether and stirred for 20 min. The biphasic mixture was partitioned in a separatory funnel. The aqueous layer was extracted twice with ether and the combined organic extracts were washed with water twice and brine once, dried over Na$_2$SO$_4$, and filtered. Concentration under reduced pressure followed by flash chromatography on silica gel (elution with 5% EtOAc/hexanes) afforded 640 mg (75% yield) of the azide as a clear oil.

To a stirring solution of the azide (640 mg, 3.42 mmol) in THF (18 mL) under N$_2$ was added PPh$_3$ (1.79 g, 6.84 mmol). Water (2.1 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over Na$_2$SO$_4$, and filtered. Concentration under reduced pressure followed by flash chromatography on silica gel (elution with 10% MeOH/CH$_2$Cl$_2$ to 20% MeOH/CH$_2$Cl$_2$ gradient) afforded 404 mg (73% yield) of amine 6 as a white solid. $^1$H NMR (CDCl$_3$, 300 MHz) δ 7.37-7.17 (m, 5H), 6.44 (d, J=15.0 Hz, 1H), 6.23-6.13 (m, 1H), 3.09-2.98 (m, 1H), 2.34-2.25 (m, 1H), 2.23-2.13 (m, 1H), 1.83 (br. s, 2H), 1.12 (d, J=6.0 Hz, 3H); $^{13}$C NMR (CDCl$_3$, 75 MHz) ppm 137.5, 132.5, 128.5, 127.4, 127.1, 126.1, 46.9, 43.6, 23.4; MS (APCI) (M+1)$^+$ 162.2, found 162.2. The hydrochloride salt had mp 147-148° C.; Anal. (C$_{11}$H$_{16}$ClN.0.1H$_2$O) C, H, N.

Example 5

(1S,3E)-1-Methyl-4-phenyl-but-3-enylamine (S-6)

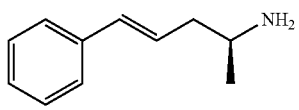

To a stirring solution of LAH (12.5 mL, 1M in THF, 12.5 mmol) in dry THF (15 mL) at 0° C. under N$_2$ was slowly added alcohol R-3 (500 mg, 3.12 mmol) in dry THF (3 mL). CAUTION: Bubbling results due to H$_2$ gas evolution. After the bubbling ceased, the reaction mixture was slowly warmed to room temperature and then refluxed for 5 h. After cooling to room temperature, then to 0° C., the reaction mixture was carefully quenched with the successive addition of 0.47 mL H$_2$O, 0.47 mL 3 M aqueous HCl, 1.4 mL H$_2$O, and 1.4 mL 3 M aqueous HCl. CAUTION: Vigorous exotherm and bubbling results due to H$_2$ gas evolution. After the bubbling ceased, the quenched reaction mixture was slowly warmed to room temperature, stirred for 30 min, and transferred to a separatory funnel. The aqueous layer was extracted twice with ether and the combined organic extracts were washed with saturated aqueous NaHCO$_3$, water, and brine, dried over Na$_2$SO$_4$, and filtered. Concentration under reduced pressure afforded 417 mg (82% yield) of the crude (E)-olefin R-5 as a clear oil.

To a stirring solution of the (E)-olefin R-5 (417 mg, 2.57 mmol) in pyridine (2 mL) at 0° C. under N$_2$ was slowly added p-toluenesulfonyl chloride (980 mg, 5.14 mmol) in pyridine (1 mL). The reaction mixture was allowed to warm to room temperature slowly and then stirred overnight. The reaction mixture was poured into an Erlenmeyer flask containing ice and 10% aqueous HCl, using CH$_2$Cl$_2$ to aid in the transfer, and stirred until it reached room temperature. The biphasic mixture was partitioned in a separatory funnel. The aqueous layer was extracted twice with CH$_2$Cl$_2$ and the combined organic extracts were washed three times with 10% aqueous HCl, once with water and once with brine, dried over Na$_2$SO$_4$, and filtered. Concentration under reduced pressure afforded the crude tosylate as a brown oil contaminated with some unreacted starting material.

To a stirring solution of the crude tosylate in DMF (8.6 mL) was added NaN$_3$ (670 mg, 10.3 mmol) and the suspension was allowed to stir vigorously overnight. The reaction mixture was poured onto water and ether and stirred for 20 min. The biphasic mixture was partitioned in a separatory funnel. The aqueous layer was extracted twice with ether and the combined organic extracts were washed with water twice and brine once, dried over Na$_2$SO$_4$, and filtered. Concentration under reduced pressure followed by flash chromatography on silica gel (elution with 5% EtOAc/hexanes) afforded 440 mg (91% yield) of the azide as a clear oil.

To a stirring solution of the azide (440 mg, 2.35 mmol) in THF (12 mL) under N$_2$ was added PPh$_3$ (1.23 g, 4.70 mmol). Water (1.5 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over Na$_2$SO$_4$, and filtered. Concentration under reduced pressure followed by flash chromatography on silica gel (elution with 10% MeOH/CH$_2$Cl$_2$ to 20% MeOH/CH$_2$Cl$_2$ gradient) afforded 190 mg (50% yield) of amine S-6 as a clear oil. [α]$^{20}_D$+24.1 g/mL (c 0.0039, MeOH); $^1$H NMR (CDCl$_3$, 300 MHz) δ 7.37-7.17 (m, 5H), 6.45 (d, J=15.0 Hz, 1H), 6.26-6.13 (m, 1H), 3.09-3.01 (m, 1H), 2.34-2.25 (m, 1H), 2.23-2.13 (m, 1H), 1.80 (br. s, 2H), 1.12 (d, J=6.0 Hz, 3H); $^{13}$C NMR (CDCl$_3$, 75 MHz) ppm 137.5, 132.5, 128.5, 127.4, 127.1, 126.1, 46.9, 43.6, 23.4; MS (APCI) (M+1)$^+$ 162.2, found 162.3. The hydrochloride salt had mp 172-173° C.; Anal. (C$_{11}$H$_{16}$ClN) C, H, N.

Example 6

(1R,3E)-1-Methyl-4-phenyl-but-3-enylamine (R-6)

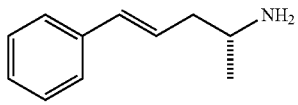

To a stirring solution of LAH (12.5 mL, 1M in THF, 12.5 mmol) in dry THF (15 mL) at 0° C. under N$_2$ was slowly added alcohol S-3 (500 mg, 3.12 mmol) in dry THF (3 mL). CAUTION: Bubbling results due to H$_2$ gas evolution. After the bubbling ceased, the reaction mixture was slowly warmed to room temperature and then refluxed for 5 h. After cooling to room temperature, then to 0° C., the reaction mixture was carefully quenched with the successive addition of 0.47 mL H$_2$O, 0.47 mL 3 M aqueous HCl, 1.4 mL H$_2$O, and 1.4 mL 3 M aqueous HCl. CAUTION: Vigorous exotherm and bubbling results due to H$_2$ gas evolution. After the bubbling ceased, the quenched reaction mixture was slowly warmed to room temperature, stirred for 30 min, and transferred to a separatory funnel. The aqueous layer was extracted twice with ether and the combined organic extracts were washed with saturated aqueous NaHCO$_3$, water, and brine, dried over Na$_2$SO$_4$, and filtered. Concentration under reduced pressure afforded 500 mg (99% yield) of the crude (E)-olefin S-5 as a white solid.

To a stirring solution of the (E)-olefin S-5 (500 mg, 3.08 mmol) in pyridine (2.1 mL) at 0° C. under N$_2$ was slowly added p-toluenesulfonyl chloride (1.17 g, 6.16 mmol) in pyridine (1 mL). The reaction mixture was allowed to warm to room temperature slowly and then stirred overnight. The reaction mixture was poured into an Erlenmeyer flask containing ice and 10% aqueous HCl, using CH$_2$Cl$_2$ to aid in the transfer, and stirred until it reached room temperature. The biphasic mixture was partitioned in a separatory funnel. The aqueous layer was extracted twice with CH$_2$Cl$_2$ and the combined organic extracts were washed three times with 10% aqueous HCl, once with water, and once with brine, dried over Na$_2$SO$_4$, and filtered. Concentration under reduced pressure afforded the crude tosylate as a brown oil contaminated with some unreacted starting material.

To a stirring solution of the crude tosylate in DMF (10 mL) was added NaN$_3$ (800 mg, 12.3 mmol) and the suspension was allowed to stir vigorously overnight. The reaction mixture was poured onto water and ether and stirred for 20 min. The biphasic mixture was partitioned in a separatory funnel. The aqueous layer was extracted twice with ether and the combined organic extracts were washed with water twice and brine once, dried over Na$_2$SO$_4$, and filtered. Concentration under reduced pressure followed by flash chromatography on silica gel (elution with 5% EtOAc/hexanes) afforded 370 mg (64% yield) of the azide as a clear oil.

To a stirring solution of the azide (370 mg, 1.98 mmol) in THF (10 mL) under N$_2$ was added PPh$_3$ (1.04 g, 3.96 mmol). Water (1.2 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over Na$_2$SO$_4$, and filtered. Concentration under reduced pressure followed by flash chromatography on silica gel (elution with 10% MeOH/CH$_2$Cl$_2$ to 20% MeOH/CH$_2$Cl$_2$ gradient) afforded 146 mg (46% yield) of amine R-6 as a clear oil. [α]$^{20}_D$-5.7 g/mL (c 0.0021, MeOH); $^1$H NMR (CDCl$_3$, 300 MHz) δ 7.38-7.20 (m, 5H), 6.45 (d, J=15.0 Hz, 1H), 6.24-6.16 (m, 1H), 3.12-3.01 (m, 1H), 2.37-2.17 (br. m, 4H), 1.15 (d, J=6.0 Hz, 3H); $^{13}$C NMR (CDCl$_3$, 75 MHz) ppm 137.4, 132.7, 128.5, 127.2, 126.1, 47.0, 43.3, 23.1; MS (APCI) (M+1)$^+$ 162.2, found 162.2. The hydrochloride salt had mp 172-174° C.; Anal. (C$_{11}$H$_{16}$ClN.0.1H$_2$O) C, H, N.

Example 7

(3Z)-1-Methyl-4-phenyl-but-3-enylamine (8)

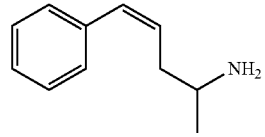

A mixture of alcohol 3 (900 mg, 5.62 mmol), Lindlar's catalyst (720 mg, 80 wt. %), and quinoline (9 mL, 76.4 mmol) in MeOH (250 mL) in a Paar bottle was shaken in a Paar hydrogenator at 43 psi for 3 h. The mixture was filtered through Celite, washed with MeOH and then concentrated under reduced pressure. The residue was dissolved in CH$_2$Cl$_2$ and 10% aqueous HCl. The biphasic mixture was partitioned in a separatory funnel. The aqueous layer was extracted twice with CH$_2$Cl$_2$ and the combined organic extracts were washed twice with 10% aqueous HCl and once with brine, dried over Na$_2$SO$_4$, and filtered. Concentration under reduced pressure afforded the crude (Z)-olefin 7 contaminated with ~10% of the fully saturated compound as a brown oil.

To a stirring solution of the crude (Z)-olefin 7 in pyridine (2 mL) at 0° C. under N$_2$ was slowly added p-toluenesulfonyl chloride (2.14 g, 11.2 mL) in pyridine (4 mL). The reaction mixture was allowed to warm to room temperature slowly and then stirred overnight. The reaction mixture was poured into an Erlenmeyer flask containing ice and 10% aqueous HCl, using CH$_2$Cl$_2$ to aid in the transfer, and stirred until it reached room temperature. The biphasic mixture was partitioned in a separatory funnel. The aqueous layer was extracted twice with CH$_2$Cl$_2$ and the combined organic extracts were washed three times with 10% aqueous HCl, once with water and once with brine, dried over Na$_2$SO$_4$, and filtered. Concentration under reduced pressure afforded 1.74 g (97% yield) of the crude tosylate as an orange oil.

To a stirring solution of the crude tosylate (1.74 g, 5.50 mmol) in DMF (18 mL) was added NaN$_3$ (1.43 g, 22.0 mmol). After stirring overnight, the reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded the azide as a clear oil which was used without any further purification.

To a stirring solution of the azide in THF (29 mL) under $N_2$ was added $PPh_3$ (2.89 g, 11.0 mmol). Water (3.4 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 5% MeOH/$CH_2Cl_2$ to 20% MeOH/$CH_2Cl_2$ gradient, then 100% MeOH) afforded 367 mg (41% yield) of amine 8 as a pale yellow oil. The hydrochloride salt had mp 115-117° C.; $^1$H NMR ($CD_3OD$, 300 MHz) δ 7.38-7.25 (m, 5H), 6.69 (d, J=12.0 Hz, 1H), 5.71-5.63 (m, 1H), 3.44-3.38 (m, 1H), 2.78-2.57 (m, 2H), 1.29 (d, J=6.0 Hz, 3H); $^{13}$C NMR ($CD_3OD$, 75 MHz) ppm 138.1, 134.1, 129.8, 129.6, 128.3, 127.4, 126.5, 49.2, 34.6, 18.5; MS (ESI) (M+1)$^+$ 162.2, found 162.2 (free base); Anal. ($C_{11}H_{16}ClN$) C, H, N.

Example 8

(1S,3Z)-1-Methyl-4-phenyl-but-3-enylamine (S-8)

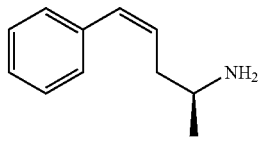

A mixture of alcohol R-3 (350 mg, 2.18 mmol), Lindlar's catalyst (280 mg, 80 wt. %), and quinoline (3.5 mL, 29.6 mmol) in MeOH (200 mL) in a Paar bottle was shaken in a Paar hydrogenator at 43 psi for 3 h. The mixture was filtered through Celite, washed with MeOH and then concentrated under reduced pressure. The residue was dissolved in $CH_2Cl_2$ and 10% aqueous HCl. The biphasic mixture was partitioned in a separatory funnel. The aqueous layer was extracted twice with $CH_2Cl_2$ and the combined organic extracts were washed twice with 10% aqueous HCl and once with brine, dried over $Na_2SO_4$, and filtered. Concentration under reduced pressure afforded the crude (Z)-olefin R-7 contaminated with ~10% of the fully saturated compound as a brown oil.

To a stirring solution of the crude (Z)-olefin R-7 in pyridine (1 mL) at 0° C. under $N_2$ was slowly added p-toluenesulfonyl chloride (831 mg, 4.36 mmol) in pyridine (1 mL). The reaction mixture was allowed to warm to room temperature slowly and then stirred overnight. The reaction mixture was poured into an Erlenmeyer flask containing ice and 10% aqueous HCl, using $CH_2Cl_2$ to aid in the transfer, and stirred until it reached room temperature. The biphasic mixture was partitioned in a separatory funnel. The aqueous layer was extracted twice with $CH_2Cl_2$ and the combined organic extracts were washed three times with 10% aqueous HCl, once with water, and once with brine, dried over $Na_2SO_4$, and filtered. Concentration under reduced pressure afforded the crude tosylate as an orange oil.

To a stirring solution of the crude tosylate in DMF (3.7 mL) was added $NaN_3$ (291 mg, 4.48 mmol). After stirring overnight, the reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded the azide as a clear oil which was used without any further purification.

To a stirring solution of the azide in THF (5.9 mL) under $N_2$ was added $PPh_3$ (588 mg, 2.24 mmol). Water (0.7 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 5% MeOH/$CH_2Cl_2$ to 20% MeOH/$CH_2Cl_2$ gradient, then 100% MeOH) afforded 118 mg (65% yield) of amine S-8 as a clear thick oil. The hydrochloride salt had mp 83-84° C.; $[\alpha]^{20}_D$ −27.9 g/mL (c 0.0014, MeOH); $^1$H NMR ($CD_3OD$, 300 MHz) δ 7.38-7.23 (m, 5H), 6.69 (d, J=12.0 Hz, 1H), 5.71-5.63 (m, 1H), 3.44-3.33 (m, 1H), 2.77-2.56 (m, 2H), 1.29 (d, J=6.0 Hz, 3H); $^{13}$C NMR ($CD_3OD$, 75 MHz) ppm 138.1, 134.1, 129.8, 129.5, 128.3, 126.5, 49.2, 34.6, 18.5; MS (ESI) (M+1)$^+$ 162.2, found 162.4; Anal. ($C_{11}H_{16}ClN \cdot 0.45H_2O$) C, H, N.

Example 9

(1R,3Z)-1-Methyl-4-phenyl-but-3-enylamine (R-8)

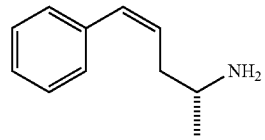

A mixture of alcohol S-3 (350 mg, 2.18 mmol), Lindlar's catalyst (280 mg, 80 wt. %), and quinoline (3.5 mL, 29.6 mmol) in MeOH (200 mL) in a Paar bottle was shaken in a Paar hydrogenator at 43 psi for 3 h. The mixture was filtered through Celite, washed with MeOH and then concentrated under reduced pressure. The residue was dissolved in $CH_2Cl_2$ and 10% aqueous HCl. The biphasic mixture was partitioned in a separatory funnel. The aqueous layer was extracted twice with $CH_2Cl_2$ and the combined organic extracts were washed twice with 10% aqueous HCl and once with brine, dried over $Na_2SO_4$, and filtered. Concentration under reduced pressure afforded the crude (Z)-olefin S-7 contaminated with ~10% of the fully saturated compound as a brown oil.

To a stirring solution of the crude (Z)-olefin S-7 in pyridine (1 mL) at 0° C. under $N_2$ was slowly added p-toluenesulfonyl chloride (831 mg, 4.36 mmol) in pyridine (1 mL). The reaction mixture was allowed to warm to room temperature slowly and then stirred overnight. The reaction mixture was poured into an Erlenmeyer flask containing ice and 10% aqueous HCl, using $CH_2Cl_2$ to aid in the transfer, and stirred until it reached room temperature. The biphasic mixture was partitioned in a separatory funnel. The aqueous layer was extracted twice with $CH_2Cl_2$ and the combined organic extracts were washed three times with 10% aqueous HCl, once with water, and once with brine, dried over $Na_2SO_4$, and filtered. Concentration under reduced pressure afforded the crude tosylate as an orange oil.

To a stirring solution of the crude tosylate in DMF (3.7 mL) was added $NaN_3$ (291 mg, 4.48 mmol). After stirring overnight, the reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded the azide as a clear oil which was used without any further purification.

To a stirring solution of the azide in THF (5.9 mL) under $N_2$ was added $PPh_3$ (588 mg, 2.24 mmol). Water (0.7 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 5% $MeOH/CH_2Cl_2$ to 20% $MeOH/CH_2Cl_2$ gradient, then 100% MeOH) afforded 102 mg (56% yield) of amine R-8 as a clear thick oil. The hydrochloride salt had mp 83-84° C.; $[\alpha]^{20}_D$ +20 g/mL (c 0.00085, MeOH); $^1H$ NMR ($CD_3OD$, 300 MHz) δ 7.38-7.22 (m, 5H), 6.69 (d, J=12.0 Hz, 1H), 5.71-5.63 (m, 1H), 3.44-3.33 (m, 1H), 2.77-2.56 (m, 2H), 1.29 (d, J=6.0 Hz, 3H); $^{13}C$ NMR ($CD_3OD$, 75 MHz) ppm 138.1, 134.1, 129.8, 129.5, 128.3, 126.5, 49.2, 34.6, 18.5; MS (ESI) $(M+1)^+$ 162.2, found 162.2 (free base); Anal. ($C_{11}H_{16}ClN\cdot0.5H_2O$) C, H, N.

Example 10

(2E)-1-Methyl-3-phenyl-prop-2-enylamine (10)

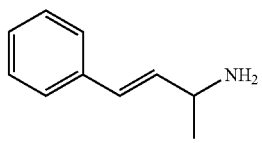

To a stirring solution of LAH (13.7 mL, 1M in THF, 13.7 mmol) in dry THF (17 mL) at 0° C. under $N_2$ was slowly added alcohol 9 (500 mg, 3.42 mmol) in dry THF (3 mL). CAUTION: Bubbling results due to $H_2$ gas evolution. After the bubbling ceased, the reaction mixture was slowly warmed to room temperature and then refluxed for 5 h. After cooling to room temperature, then to 0° C., the reaction mixture was carefully quenched with the successive addition of 0.52 mL $H_2O$, 0.52 mL 3 M aqueous HCl, 1.6 mL $H_2O$, and 1.6 mL 3 M aqueous HCl. CAUTION: Vigorous exotherm and bubbling results due to $H_2$ gas evolution. After the bubbling ceased, the quenched reaction mixture was slowly warmed to room temperature, stirred for 30 min, and transferred to a separatory funnel. The aqueous layer was extracted twice with ether and the combined organic extracts were washed with saturated aqueous $NaHCO_3$, water, and brine, dried over $Na_2SO_4$, and filtered. Concentration under reduced pressure afforded the crude (E)-olefin as a clear oil.

To a stirring solution of the crude (E)-olefin in $CH_2Cl_2$ (34 mL) at 0° C. under $N_2$ was added $NEt_3$ (0.95 mL, 6.84 mmol) and MsCl (0.40 mL, 5.13 mmol). The reaction mixture was stirred at 0° C. for 1 h and then at room temperature for 1 h after which it was quenched with saturated aqueous $NaHCO_3$ and diluted with water and $CH_2Cl_2$. The biphasic mixture was partitioned in a separatory funnel. The aqueous layer was extracted twice with $CH_2Cl_2$ and the combined organic extracts were washed with water and brine, dried over $Na_2SO_4$, and filtered. Concentration under reduced pressure afforded the crude mesylate as a brown oil which was used without any purification.

To a stirring solution of the crude mesylate in DMF (11 mL) was added $NaN_3$ (891 mg, 13.7 mmol). After stirring overnight, the reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded 570 mg (96% yield) of the azide as a clear oil.

To a stirring solution of the azide (570 mg, 3.29 mmol) in THF (17.3 mL) under $N_2$ was added $PPh_3$ (1.73 g, 6.58 mmol). Water (2.1 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 5% $MeOH/CH_2Cl_2$ to 20% $MeOH/CH_2Cl_2$ gradient, then 100% MeOH) afforded 70 mg (14% yield) of amine 11 as a clear oil. $^1H$ NMR ($CDCl_3$, 300 MHz) δ 7.38-7.20 (m, 5H), 6.48 (d, J=18.0 Hz, 1H), 6.20 (dd, J=15.0, 6.0 Hz, 1H), 3.72-3.64 (m, 1H), 2.00 (br. s, 2H), 1.26 (d, J=6.0 Hz, 3H); $^{13}C$ NMR ($CDCl_3$, 75 MHz) ppm 135.7, 128.5, 128.2, 127.3, 126.3, 49.3, 23.7; MS (ESI) $(M+1)^+$ 148.2, found 146.2. The hydrochloride salt had mp 151-152° C.; Anal. ($C_{10}H_{14}ClN$) C, H, N.

Example 11

(2Z)-1-Methyl-3-phenyl-prop-2-enylamine (11)

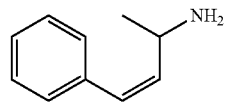

A mixture of alcohol 9 (100 mg, 0.684 mmol), Lindlar's catalyst (80 mg, 80 wt. %), and quinoline (1.1 mL, 9.31 mmol) in MeOH (100 mL) in a Paar bottle was shaken in a Paar hydrogenator at 43 psi for 4 h. The mixture was filtered through Celite and then concentrated under reduced pressure. The residue was dissolved in $CH_2Cl_2$ and 10% aqueous HCl. The biphasic mixture was partitioned in a separatory funnel. The aqueous layer was extracted twice with $CH_2Cl_2$ and the combined organic extracts were washed twice with 10% aqueous HCl and once with brine, dried over $Na_2SO_4$, and filtered. Concentration under reduced pressure afforded the crude (Z)-olefin contaminated with ~10% of the fully saturated compound as a brown oil.

To a stirring solution of the crude (Z)-olefin in $CH_2Cl_2$ (6.8 mL) at 0° C. under $N_2$ was added $NEt_3$ (0.19 mL, 1.36 mmol) and MsCl (0.16 mL, 2.04 mmol). The reaction mixture was stirred at 0° C. for 1 h and then at room temperature for 1 h after which it was quenched with saturated aqueous $NaHCO_3$ and diluted with water and $CH_2Cl_2$. The biphasic mixture was partitioned in a separatory funnel. The aqueous layer was extracted twice with $CH_2Cl_2$ and the combined organic extracts were washed with water and brine, dried over $Na_2SO_4$, and filtered. Concentration under reduced pressure afforded the crude mesylate as a brown oil which was used without any purification.

To a stirring solution of the crude mesylate in DMF (2.3 mL) was added $NaN_3$ (177 mg, 2.73 mmol). After stirring overnight, the reaction mixture was poured onto water and ether and stirred for 20 min. The biphasic mixture was partitioned in a separatory funnel. The aqueous layer was extracted twice with ether and the combined organic extracts were washed with water twice and brine once, dried over $Na_2SO_4$, and filtered. Concentration under reduced pressure followed by flash chromatography on silica gel (elution with 5% EtOAc/hexanes) afforded 118 mg (100% yield) of the azide as a clear oil.

To a stirring solution of the azide (118 mg, 0.682 mmol) in THF (3.6 mL) under $N_2$ was added $PPh_3$ (357 mg, 1.36 mmol). Water (0.43 mL) was then added dropwise and the reaction mixture was stirred overnight. The reaction mixture was diluted with ethyl acetate and water. The biphasic mixture was partitioned in a separatory funnel. The aqueous layer was extracted twice with EtOAc and the combined organic extracts were washed with water and brine, dried over $Na_2SO_4$, and filtered. Concentration under reduced pressure followed by flash chromatography on silica gel (elution with 5% $MeOH/CH_2Cl_2$ to 20% $MeOH/CH_2Cl_2$ gradient, then 100% MeOH) afforded 46.2 mg (46% yield) of amine 12 as a clear oil. The hydrochloride salt had mp 149-151° C.; $^1H$ NMR ($CD_3OD$, 300 MHz) δ 7.48-7.45 (m, 2H), 7.37-7.28 (m, 3H), 6.77 (d, J=15.0 Hz, 1H), 6.26 (dd, J=15.0, 6.0 Hz, 1H), 4.11-4.02 (m, 1H), 1.50 (d, J=9.0 Hz, 3H); $^{13}C$ NMR ($CD_3OD$, 75 MHz) ppm 137.1, 135.5, 129.8, 129.6, 127.8, 126.9, 50.7, 19.6; MS (APCI) $(M+1)^+$ 148.2, found 146.3 (free base); Anal. ($C_{10}H_{14}ClN$) C, H, N.

Example 12

Biological Assays

Dopamine Transporter (DAT), Norepinephrine Transporter (NET), and Serotonin Transporter (SERT) Assays All animal studies were conducted in facilities fully accredited by the Association for the Assessment and Accreditation of Laboratory Animal Care (AAALAC) and experiments were performed in accordance with the Institutional Care and Use Committee (IACUC) of the National Institute on Drug Abuse Intramural Research Program (NIDA IRP). Rats were euthanized by $CO_2$ narcosis, and brains were processed to yield synaptosomes as previously described (Rothman, R B, et al., *Eur. J. Pharmacol.* 2002, 447(1), 51.). Synaptosomes were prepared from rat striatum for the DAT assays, whereas synaptosomes were prepared from whole brain minus striatum and cerebellum for the NET and SERT assays.

For uptake inhibition assays, 5 nM [$^3$H]DA, 10 nM [$^3$H]norepinephrine (NE) and 5 nM [$^3$H]5-HT were used to assess transport activity at DAT, NET, and SERT, respectively. The selectivity of uptake assays was optimized for a single transporter by including unlabeled blockers to prevent uptake of [$^3$H]transmitter by competing transporters. Uptake inhibition assays were initiated by adding 100 μl of tissue suspension to 900 μL Krebs-phosphate buffer (126 mM NaCl, 2.4 mM KCl, 0.83 mM $CaCl_2$, 0.8 mM $MgCl_2$, 0.5 mM $KH_2PO_4$, 0.5 mM $Na_2SO_4$, 11.1 mM glucose, 0.05 mM pargyline, 1 mg/mL bovine serum albumin, and 1 mg/mL ascorbic acid, pH 7.4) containing test drug and [$^3$H]transmitter. Uptake inhibition assays were terminated by rapid vacuum filtration through Whatman GF/B filters, and retained radioactivity was quantified by liquid scintillation counting. Concentration-response curves were generated to yield $IC_{50}$ values.

For release assays, 9 nM [$^3$H]1-methyl-4-phenylpyridinium ([$^3$H]MPP+) was used as the radiolabeled substrate for DAT and NET, while 5 nM [$^3$H]5-HT was used as a substrate for SERT. All buffers used in the release assay methods contained 1 μM reserpine to block vesicular uptake of substrates. The selectivity of release assays was optimized for a single transporter by including unlabeled blockers to prevent the uptake of [$^3$H]MPP+ or [$^3$H]5-HT by competing transporters. Synaptosomes were preloaded with radiolabeled substrate in Krebs-phosphate buffer for 1 h (steady state). Release assays were initiated by adding 850 μL of preloaded synaptosomes to 150 μL of test drug. Release was terminated by vacuum filtration and retained radioactivity was quantified as described for uptake inhibition. Concentration-response curves were generated to yield $EC_{50}$ values.

Substrate reversal experiments were conducted to validate substrate activity. The releasing ability of test compounds was tested at an $EC_{80}$ concentration in the absence and presence of an uptake inhibitor (250 nM GBR1209 for DAT, 166 nM desipramine for NET, 100 nM fluoxetine for SERT). If the test agent was a releaser, the uptake inhibitor reduced the effect of the test agent. If the test agent was an uptake inhibitor, the addition of a second uptake inhibitor led to either no change or an increased effect in the release assay.

Calcium Mobilization Assays.

HEK293 cells stably expressing the human $5-HT_{2A}$ receptor were used. The day before the assay, cells were plated into 96-well black-walled assay plates at 40,000 cells/well in DMEM-HG supplemented with 10% fetal bovine serum, 100 units of penicillin and streptomycin, and 15 mM HEPES. The cells were incubated overnight at 37° C., 5% $CO_2$. Prior to the assay, Calcium 5 dye (Molecular Devices) was reconstituted according to the manufacturer instructions. The reconstituted dye was diluted 1:40 in pre-warmed (37° C.) assay buffer (1×HBSS, 20 mM HEPES, 2.5 mM probenecid, pH 7.4 at 37° C.). Growth medium was removed and the cells were gently washed with 100 μL of pre-warmed (37° C.) assay buffer. The cells were incubated for 45 minutes at 37° C., 5% $CO_2$ in 200 μL of the diluted Calcium 5 dye. Serial dilutions of the test compounds were prepared in 1% DMSO/assay buffer, aliquoted into 96-well polypropylene plates, and warmed to 37° C. After the dye-loading incubation period, the cells were pre-treated with 25 μL of 9% DMSO/assay buffer and incubated for 15 min at 37° C. After the pre-treatment incubation period, the plate was read with a FlexStation® II (Molecular Devices). Calcium-mediated changes in fluorescence were monitored every 1.52 seconds over a 60 second time period, with the FlexStation® II adding 25 μL of test compound dilutions at the 19 second time point (excitation at 485 nm, detection at 525 nm). Peak kinetic reduction (SoftMax, Molecular Devices) relative fluorescent units (RFU) were plotted against compound concentration. Data were fit to the appropriate three-parameter logistic curve to generate $EC_{50}$ values (GraphPad Prism 6.0, GraphPad Software, Inc., San Diego, Calif.). $5\text{-}HT_{2B}$ and $5\text{-}HT_{2C}$ calcium mobilization assays were run in the same manner with stable $5\text{-}HT_{2B}$ and $5\text{-}HT_{2C}$ HEK293 cells except that 35,000 cells/well were used instead of 40,000 cells/well. The results are set forth in Table 1, above.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure correspondingly contemplates such features, aspects and embodiments, or a selected one or ones thereof, in various permutations and combinations, as being within the scope of the present disclosure.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the claimed is intended to be broadly construed and interpreted, as including all such variations, modifications and alternative embodiments, within its spirit and scope.

What is claimed is:

1. A method of mediating dopamine transporter (DAT) and norepinephrine transporter (NET) activity with a substrate type releaser, said method comprising administering to a subject in need thereof a therapeutically effective amount of a compound according to the structure of Formula I:

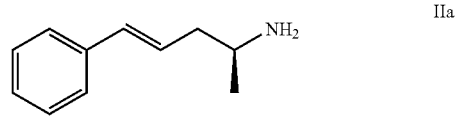

wherein A is $C_{3\text{-}4}$ alkynyl or $C_{2\text{-}4}$ alkenyl; $R^1\text{-}R^5$ and $R^9$ are each independently selected from H, OH, optionally substituted $C_{1\text{-}3}$ alkyl, optionally substituted $C_{1\text{-}2}$ alkoxy, optionally substituted $C_{2\text{-}3}$ alkenyl, optionally substituted $C_{2\text{-}3}$ alkynyl, halo, amino, CN, $CF_3$, and $NO_2$; and $R^{10}$ and are H or $C_{1\text{-}3}$ alkyl; or a pharmaceutically acceptable ester, amide, salt, solvate, prodrug, or stereoisomer thereof.

2. The method according to claim 1, wherein A is $C_{2\text{-}4}$ alkenyl.

3. The method according to claim 2, wherein the compound is represented by the structure of formula II:

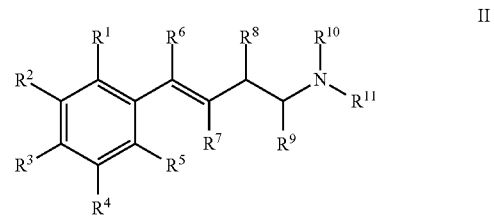

wherein $R^6$ and Ware each independently selected from H or $C_{1\text{-}3}$ alkyl and $R^8$ is selected from H, OH, optionally substituted $C_{1\text{-}3}$ alkyl, optionally substituted $C_{1\text{-}2}$ alkoxy, optionally substituted $C_{2\text{-}3}$ alkenyl, optionally substituted $C_{2\text{-}3}$ alkynyl, halo, amino, CN, $CF_3$, and $NO_2$; or a pharmaceutically acceptable ester, amide, salt, solvate, prodrug, or stereoisomer thereof.

4. The method according to claim 3, wherein $R^{10}$ and $R^{11}$ are H.

5. The method according to claim 3, wherein the compound is selected from (3E)-1-Methyl-4-phenyl-but-3-enylamine, (3Z)-1-Methyl-4-phenyl-but-3-enylamine and stereoisomers thereof.

6. The method according to claim 3, wherein the compound is represented by formula IIa:

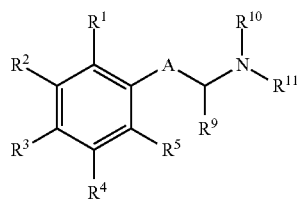

or a pharmaceutically acceptable ester, amide, salt, solvate, prodrug, or stereoisomer thereof.

7. The method according to claim 1, wherein A is $C_{3\text{-}4}$ alkynyl.

8. The method according to claim 1, wherein A is $C_3$ alkynyl and $R^{10}$ and $R^{11}$ are H.

9. The method according to claim 1, wherein the compound is a serotonin transmitter (SERT) releaser.

10. A method of mediating dopamine transporter (DAT) and norepinephrine transporter (NET) activity with a substrate type releaser, said method comprising administering to a subject in need thereof a therapeutically effective amount of a compound according to the structure of Formula II:

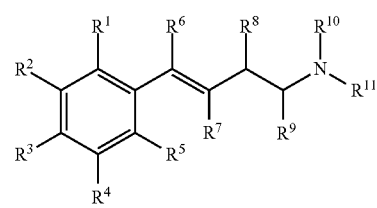

$R^1\text{-}R^5$ and $R^9$ are each independently selected from H, OH, optionally substituted $C_{1\text{-}3}$ alkyl, optionally substituted $C_{1\text{-}2}$ alkoxy, optionally substituted $C_{2\text{-}3}$ alkenyl, optionally substituted $C_{2\text{-}3}$ alkynyl, halo, amino, CN, $CF_3$, and $NO_2$; $R^6$ and $R^7$ are each independently selected from H or $C_{1\text{-}3}$ alkyl; $R^8$ is selected from H, OH, optionally substituted $C_{1\text{-}3}$ alkyl, optionally substituted $C_{1\text{-}2}$ alkoxy, optionally substituted $C_{2\text{-}3}$ alkenyl, optionally substituted $C_{2-3}$ alkynyl, halo, amino, CN, $CF_3$, and $NO_2$; and $R^{10}$ and $R^{11}$ are H or $C_{1-3}$ alkyl; or a pharmaceutically acceptable ester, amide, salt, solvate, prodrug, or stereoisomer thereof.

11. The method of claim 10, wherein the compound is represented by formula IIa:

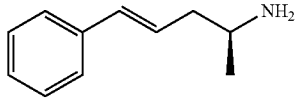

IIa

Zone Name: or a pharmaceutically acceptable ester, amide, salt, solvate, prodrug, or stereoisomer thereof.

12. The method of claim 10, wherein the compound is a serotonin transmitter (SERT) releaser.

* * * * *

UNITED STATES PATENT AND TRADEMARK OFFICE
CERTIFICATE OF CORRECTION

PATENT NO. : 10,899,699 B2
APPLICATION NO. : 16/300436
DATED : January 26, 2021
INVENTOR(S) : Bruce Blough et al.

It is certified that error appears in the above-identified patent and that said Letters Patent is hereby corrected as shown below:

In the Specification

Column 1, Lines 4-7 should read as follows:
-- This is a U.S. national phase of International Patent Application PCT/US 17/32143 filed May 11, 2017, which in turn claims the benefit of priority of U.S. Provisional Application No. 62/335,191 filed May 12, 2016. The disclosures of International Patent Application PCT/US17/32143 and U.S. Provisional Application No. 62/335,191 are hereby incorporated herein by reference in their respective entireties --.

Column 9, Line 22, "wherein $R^6$ and IC are each independently selected" should be -- wherein $R^6$ and $R^7$ are each independently selected --.

In the Claims

In Claim 1, at Column 35, Line 60, "and $R^{10}$ and are H or $C_{1-3}$ alkyl" should be -- and $R^{10}$ and $R^{11}$ are H or $C_{1-3}$ alkyl --.

In Claim 3, at Column 36, Line 12, "wherein $R^6$ and Ware each independently selected from H" should be -- wherein $R^6$ and $R^7$ are each independently selected from H --.

In Claim 11, at Column 37, Line 15, "Zone Name:" should be deleted.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*